United States Patent [19]

Barchas et al.

[11] Patent Number: 4,587,233
[45] Date of Patent: May 6, 1986

[54] USE OF ARG-PHE-AMIDE DERIVATIVES

[75] Inventors: Jack D. Barchas, Stanford; Eckard Weber; Christopher J. Evans, both of Palo Alto; E. T. Wei, El Cerrito; J. K. Chang, San Carlos, all of Calif.; Ingbert Fuchs; Gabriele Mues, both of De Soto, Tex.

[73] Assignee: Board of Trustees of the Leland Stanford Junior University, Stanford, Calif.

[21] Appl. No.: 549,961

[22] Filed: Nov. 7, 1983

[51] Int. Cl.$^4$ .............................................. A61K 37/00
[52] U.S. Cl. ...................................... 514/15; 514/16; 514/17; 514/18; 514/19
[58] Field of Search ................. 260/112.5 E, 112.5 R; 514/15, 16, 17, 18, 19

[56] References Cited

U.S. PATENT DOCUMENTS 4,152,322  5/1979  Freidinger ................... 260/112.5 R
4,264,492  4/1981  Stein ............................ 260/112.5 E

OTHER PUBLICATIONS

Biochem. and Biophys. Res. Commun. 96, (1980), 1393–1399.
Synthetic Peptides, vol. 3 (1978), 116, 117.
Synthetic Peptides, vol. 2 (1978), 40, 41.
Synthetic Peptides, vol. 6 (1984), 172, 173.
Chem. Abstr. vol. 100, (1984) 2886a.
Chem. Abstr. vol. 100, (1984) 988m.
Chem. Abstr. vol. 97, (1982) 107544k.
Chem. Abstr. vol. 97 (1982) 107476q.
Chem. Abstr. vol. 97 (1982) 121128j.
Chem. Abstr. vol. 97, (1982) 36394.
Chem. Abstr. vol. 95, (1981) 217900q.
Chem. Abstr. vol. 95, (1981) 144325u.
Chem. Abstr. vol. 93, (1980) 23048f.
Chem. Abstr. vol. 81, (1974) 35754y.
Chem. Abstr. vol. 87, (1977) 113476z.
Chem. Abstr. vol. 77, (1972) 149838b.
Chem. Abstr. vol. 73, (1970) 22806b.
Chem. Abstr. vol. 99, (1983) 206235h.
Chem. Abstr. vol. 99, (1983) 192063m.
Chem. Abstr. vol. 99, (1983) 169752b.
Chem. Abstr. vol. 99, (1983) 64854h.
Chem. Abstr. vol. 100, (1984) 62168.
Chem. Abstr. vol. 98, (1983) 155309.
Chem. Abstr. vol. 95, (1981) 39661.
Chem. Abstr. vol. 95, (1981) 110403.
Chem. Abstr. vol. 66, (1967) 42119p.
Chem. Abstr. vol. 85, (1976) 117514s.
Chem. Abstr. vol. 92, (1980) 187946.

*Primary Examiner*—Delbert R. Phillips
*Attorney, Agent, or Firm*—Flehr, Hohbach, Test, Albritton & Herbert

[57] ABSTRACT

A method is provided for elevating blood pressure in mammals comprising the step of administering a polypeptide containing the C-terminal residue L-Arg-L-Phe or C-terminal esters or amides thereof.

4 Claims, 4 Drawing Figures

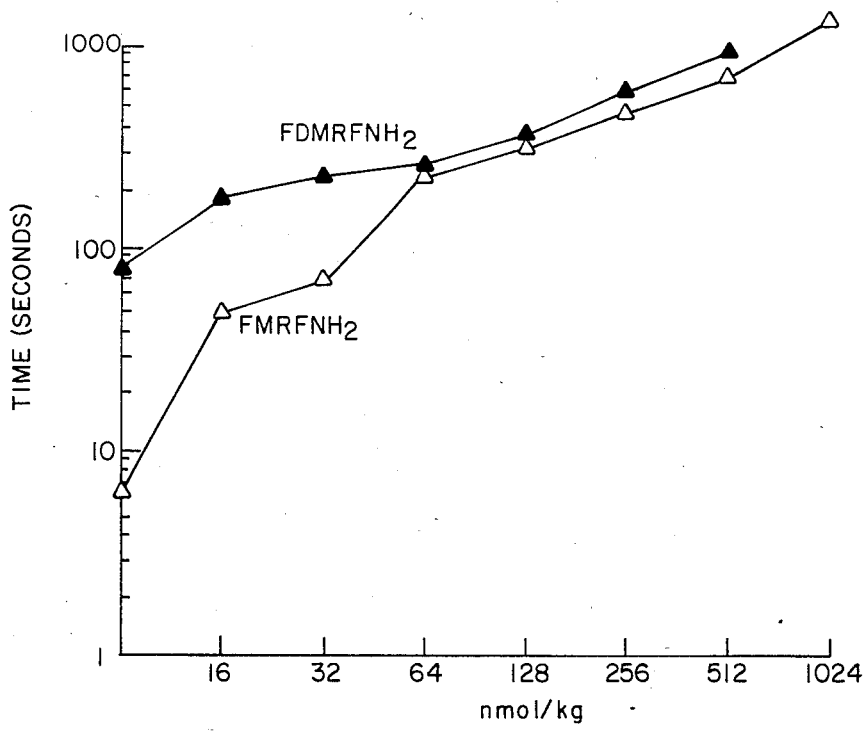
FIG.—2B
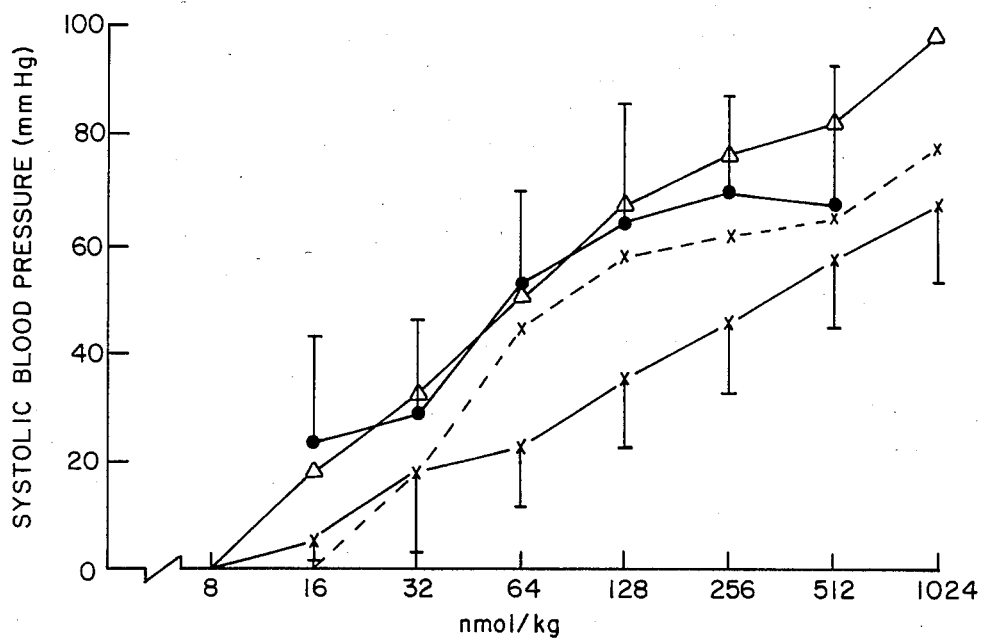
FIG.—3

USE OF ARG-PHE-AMIDE DERIVATIVES

The invention disclosed herein was made in the course of work under Grant No. DA-00091 from the Department of Health and Human Services and under Contract No. N00014-79-C-0796 from the Office of Naval Research. The United States Government has rights to the invention pursuant to these grants.

The present invention is directed to a method of elevating blood pressure in mammals.

It is an object of the present invention to provide a method for elevating blood pressure in mammals and polypeptides useful therefor.

It is a further object of the present invention to provide novel compositions which may administered to mammals to elevate blood pressure.

These and other objects will become apparent to those of ordinary skill in the art from the following description and claims.

In the accompanying figures:

FIG. 2A shows the dose response and FIG. 2B shows the time response relative to dosage for the pressor effects of four exemplary polypeptides according to the present invention when administered to anesthetized rats.

FIG. 3 shows the dose response relative to for the pressor effect (systolic blood pressure) of a preferred polypeptide according to the present invention as compared among normal rats, adrenalectomized rats, sham hypophysectomized rats and hypophysectomized rats.

Figure 1:
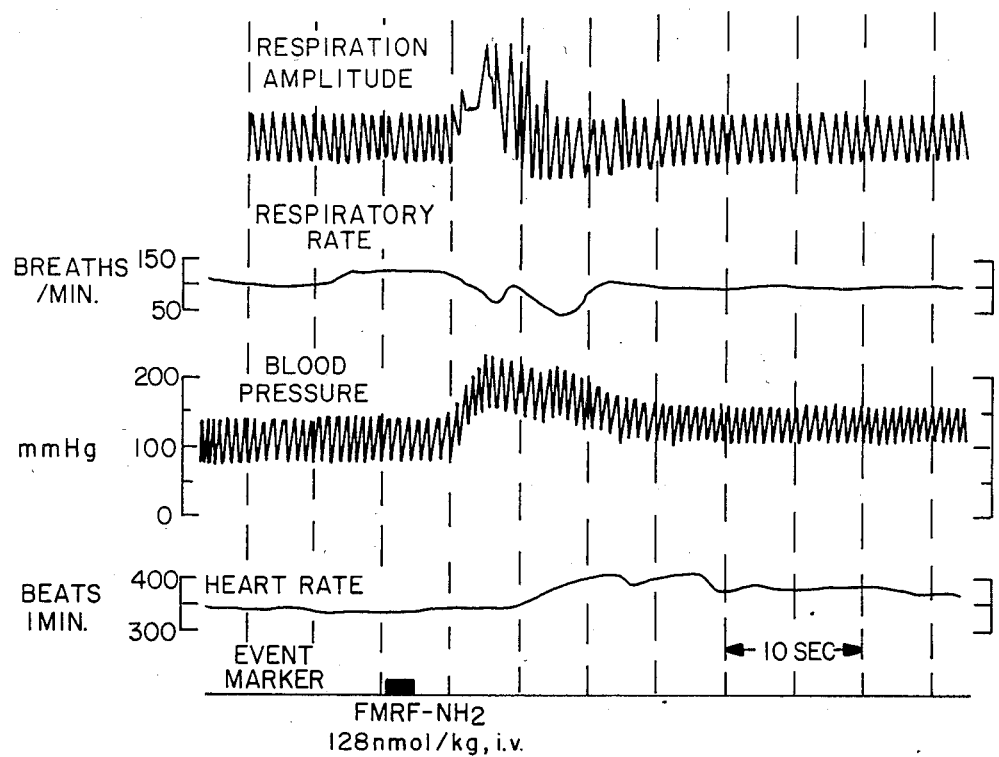
FIG. 1 is a graph illustrating the effects of a preferred polypeptide according to the present invention on the respiration, respiratory rate, blood pressure and heart rate in an anesthetized rat.

The endogenous opiate receptor ligand met-enkephalin is widely distributed in the central and peripheral nervous systems of invertebrates and vertebrates. Metenkephalin may be biosynthetically derived from a number putative precursor peptides, one of which has the amino acid sequence Tyr-Gly-Gly-Phe-Met-Arg-Phe. See Stern et al., PNAS USA 76, 6680 (1979). The carboxy terminal tetrapeptide fragment of the aforementioned heptapeptide is identical to the amidated molluscan cardioexcitatory peptide Phe-Met-Arg-Phe-NH$_2$ which is isolated from clam ganglia (Price et al., *Science*, 197, 670 (1977)). Furthermore, the rodent brain contains a neuronal system which is specifically labelled by antibodies raised to Phe-Met-Arg-Phe-NH$_2$. See Dockray et al., *Nature*, 293, 656-657 (1981); and Weber et al., *Science*, 214, 1248-1251 (1981).

We have now found that Phe-Met-Arg-Phe-NH$_2$ and other polypeptides containing the carboxy terminal residues L-Arg-L-Phe, or C-terminal esters or amides thereof, when injected intravenously into mammals, demonstrate a potent stimulating effect on blood pressure. We have further found that this effect is stereospecific and is dependent upon the presence of the carboxy terminal L-Arg-L-Phe configuration.

We have discovered a novel method for elevating blood pressure in mammals comprising the step of administering an effective amount of a compound sufficient to induce blood pressure elevation, such compound selected from a polypeptide containing the carboxy terminal residue L-Arg-L-Phe, or C-terminal esters or amides thereof. We have also discovered a novel class of polypeptides which are useful for elevating blood pressure in mammals, which peptides contain up to eleven amino acids and are selected from those containing the C-terminal residues L-Arg-L-Phe, or C-terminal esters or amides thereof, with the proviso that the polypeptide is not L-Phe-L-Met-L-Arg-L-Phe-NH$_2$ or L-Tyr-Gly-Gly-L-Phe-L-Met-L-Arg-L-Phe.

We have found that generally polypeptides having the two C-terminal residues L-Arg-L-Phe, or C-terminal esters or amides thereof, will elevate the blood pressure in mammals. While it is not believed to be any critical limit to the length of the polypeptide, a preferred class of polypeptides comprises those having up to eleven amino acids. For example, the gamma 1-melanotropic stimulating hormone (gamma-MSH), a polypeptide containing eleven amino acid residues and having an L-arginine-L-phenylalaninamide C-terminus exhibits pressor activity.

Another preferred class of compounds comprise polypeptides containing up to seven amino acids. Any of the amino acid residues may be of the D configuration as well as the naturally occurring L configuration, except for the last two amino acids on the C-terminus which must be of the L configuration. For example, peptides such as Tyr-Gly-Gly-Phe-Met-Arg-Phe-NH$_2$ having an all L configuration or in which any or all of the amino acid residues in the first, fourth, or fifth positions are in the D configuration are within the scope of the present invention.

A more preferred class of polypeptides according to the present invention, comprise polypeptides containing up to four amino acids wherein the C-terminal residues are L-Arg-L-Phe, or C-terminal esters or amides thereof. Polypeptides included in this class include D-Phe-L-Met-L-Arg-L-Phe-NH$_2$, L-Phe-D-Met-L-Arg-L-Phe-NH$_2$, D-Phe-D-Met-L-Arg-L-Phe-NH$_2$, L-Met-L-Arg-L-Phe-NH$_2$, or C-terminal esters or other substituted amides thereof. The most preferred compound in this class for use for blood pressure elevation is the known tetrapeptide Phe-Met-Arg-Phe-NH$_2$.

The minimum size of the polypeptides according to the present invention comprise the dipeptide L-Arg-L-Phe, and its C-terminal esters or amides.

The polypeptides according to the present invention may be prepared utilizing conventional solid phase synthesis methods and purified by conventional methods, for example, by countercurrent distribution, thin layer chromatography, high voltage electrophoresis, HPLC and the like. Alternatively, the peptides may be synthesized on automatic peptide synthesizing machines which are commercially available. Suitable side group protecting agents, amino acid coupling agents and conditions for deprotection of side groups are well known to those of ordinary skill in the peptide art. Generally, the C-terminal amino acid residue of the desired polypeptide is linked to a resin through its carboxyl group while the amino group and appropriate side groups are protected by known protecting groups. The amino protecting group is then removed and coupled via an amide linkage to the second amino acid residue from the C-terminal end using a conventional coupling agent such as dicyclohexylcarbodiimide (DCC). In this manner each amino acid is sequentially added to form the peptide chains having the desired length and sequence with the final peptide being cleaved from the resin by an appropriate reagent such as HF, and any side chain protecting groups removed to form the final polypeptide. When the final peptide is cleaved from the resin, depending on the cleavage conditions, the C-terminal acid or amide may be formed in situ. The crude polypeptide may then be purified by conventional methods.

The polypeptides according to the present invention, particularly when injected intravenously into a mammal, are potent in raising both the systolic and diastolic blood pressure of mammals at doses of less than one micromole per kilogram of body weight. The increase in blood pressure is dose-dependent and changes by as much as 100 millimeters mercury (systolic) and 75 millimeters mercury (diastolic) may be attainable at doses of from 10–60 nmol (per kilogram) body weight. The duration of the blood pressure elevation is also dose dependent and may last from about a few seconds to several minutes. In the usual case, elevations of blood pressure may be accompanied by alterations in the heart rate and breathing as shown in FIG. 1. Typically, heart rate may be increased by about 50–100 beats per minute in a small animal.

The polypeptides according to the present invention may be admixed with conventional pharmaceutical carriers such as saline and the like and administered intravenously. The pressor effects are dose dependent, therefore the dosage which may be administered will depend upon the degree to which it is desirable to raise the animals blood pressure. Elevation in blood pressure may be obtained by intravenous injection of dosages of less than one micromole per kilogram body weight. Preferably dosages in the range of 10–60 nmol-per kilogram body weight may be used.

Having provided the above description of the invention, the following examples are illustrative but are not intended to limit the scope of the invention.

EXAMPLE 1

Solid-Phase Synthesis of Phe-Met-Arg-Phe-NH$_2$

Boc-Phe (1.75 g, 6 mM) was coupled to p-Methylbenzhydryllamine (p-Me-BHA)-resin (4.6 g, 2 mM) with 3 molar excess of dicyclohexylcarbodiimide (DCC, 0.5M in methylene chloride, 12 ml.) for one hour in 5% dimethylformamide (DMF)/CH$_2$Cl$_2$ solution. The resulting Boc-Phe-P-Me-BHA resin was washed well with CH$_2$Cl$_2$ and acetylated with acetic anhydride and triethlamine (Et$_3$N) in CH$_2$Cl$_2$ for 20 minutes. This resin was then washed three times with CH$_2$Cl$_2$.

Further synthesis was done manually with a Peninsula Manual Synthesizer (Peninsula Laboratories, San Carlos, Calif. by:
(1) Prewashed with 33% trifluoroacetic acid (TFA) in CH$_2$Cl$_2$ containing 1% indole for one minute.
(2) Deprotection with 33% TFA in CH$_2$Cl$_2$ for 20 minutes.
(3) Washed with CH$_2$Cl$_2$ once for one minute.
(4) Washed with EtOH once for one minute.
(5) Washed with CH$_2$Cl$_2$ twice for one minute.
(6) Prewashed with 10% triethylamine in CH$_2$Cl$_2$ for one minute.
(7) Neutralization with 10% Et$_3$N in CH$_2$Cl$_2$ for 10 minutes.
(8) Washed with CH$_2$Cl$_2$ three times for one minute.
(9) Protected t-butyloxycarbonyl (Boc)-amino acid (3 molar excess) in 5% DMF in CH$_2$Cl$_2$ was added.
(10) DCC (0.5M in CH$_2$Cl$_2$, 12 ml.) was added and the reaction time was up to two hours.
(11) Washed with CH$_2$Cl$_2$ three times for one minute. Completion of the coupling step was monitored by ninhydrin test. The side chain guanidine group of Arg was protected by a tosyl (Tos) group.

After four cycles, the peptide resin was washed with methanol and dried in vacuo overnight. This peptide resin was cleaved by HF (10 ml. HF and 2.5 ml. of anisole per gram of resin) at 0° C. for one hour. The HF was removed by vacuum and the resin was washed with anhydrous ether. The peptide was extracted by 10% HOAc solution and filtered. The filtrate was lyophilized to give the crude Phe-Met-Arg-Phe-NH$_2$.

Crude Phe-Met-Arg-Phe-NH$_2$ (1.3 g) was purified by countercurrent distribution using n-BuOH:HOAc:H$_2$O (4:1:5) system for 200 transfers. The peptide was located by spotting on a silica gel thin-layer chromatography plate and was developed with the upper layer of n-BuOH:HOAc:H$_2$O and sprayed with ninhydrin reagent. The peptide was pooled from tubes #50–70 and was evaporated to dryness. The peptide was then lyophilized to afford pure Phe-Met-Arg-Phe-NH$_2$ (0.35 g.).

Thin-layer chromatography showed $R_f$ 0.82 (cellulose glass plate, n-BuOH:Pyridine-HOAc:H$_2$O 15:10:3:12) and $R_f$ 0.75 (cellulose glass plate, n-BuOH:Pyridine:HOAc:H$_2$O 42:24:4:30). Movement on electrophoresis was $R_f$ 1.32 with reference to picric acid toward the cathode. (Whatman 3MM paper, pH 6.4 pyridine-acetate buffer, 3000 V for 30 minutes). Amino acid analysis showed correct composition with experimental error. (6N HCl at 110° C. for 20 hours in vacuo. NH$_3$ 0.91, Arg 0.99, Met 1.01 and Phe 2.01).

EXAMPLE 2

Synthesis and Purification of Tyr-Gly-Gly-Phe-Met-Arg-Phe-NH$_2$ p-Methylbenzhydrylamine (p-Me-BHA) resin (3 mM) was used as the solid-support and the synthesis, HF cleavage and countercurrent distribution was performed as described in the synthesis of Phe-Met-Arg-Phe-NH$_2$. The phenolic group of Tyr was protected by o-bromo-carbobenzoxy group.

The partially purified Tyr-Gly-Gly-Phe-Met-Arg-Phe-NH$_2$ from countercurrent distribution (0.33 g) was loaded onto a G-25 column (2.5×30 cm) and used the partition phase of n-BuOH:HOAc:H$_2$O (4:1:5) as the eluting solvent to afford 0.24 g of peptide. This peptide was further purified by a CM cellulose ion-exchange column eluted with a linear gradient buffer of 0.05M to 0.2M NH$_4$OAc solution to give pure Tyr-Gly-Gly-Phe-Met-Arg-Phe-NH$_2$ (0.19 g). Thin-layer Chromatography showed $R_f$ 0.62 (silica gel glass plate, EtOAc:n-BuOH:HOAc:H$_2$O 15:10:3:12). Movement on electrophoresis was $R_f$ 0.95 with reference to picric acid toward the cathode (Whatman 3MM paper, pH 6.4 pyridine-acetate buffer, 3000 V for 30 minutes). Amino acid analysis showed correct composition with experimental error. (6N HCl at 110° C. for 20 hours in vacuo. NH$_3$ 1.22, Arg 0.98, Gly 2.03, Met 0.98, Tyr 1.00 and Phe 2.01).

EXAMPLE 3

Synthesis and Purification of Tyr-Gly-Gly-Phe-Met-Arg-Phe

Synthesis, HF cleavage and countercurrent distribution of this peptide was performed as described in Example 2 except that the resin used was Boc-Phe-benzyl ester resin. (2 mN, 4.45 g). 0.88 g of pure peptide was collected. Thin-layer chromatography showed $R_f$ 0.61 (silica gel glass plate, n-BuOH:EtOAc:HOAc:H$_2$O 1:1:1:1.) and $R_f$ 0.44 (silica gel, n-BuOH:pyridine:-

HOAc:H₂O 15:10:3:12). Movement on electrophoresis was $R_f$ 0.68 with reference to picric acid toward the cathode. (Whatman 3MM paper, pyridine-acetate 1H 6.4 buffer, 3000 V for 30 minutes.). Amino acid analysis: 6N HCl at 110° C. for 20 hours in vacuo. Arg 1.03, Gly 1.96, Met 0.96, Tyr 0.95 and Phe 1.87.

EXAMPLE 4

Synthesis and purification of Phe-Met-Arg-Phe

Pure Phe-Met-Arg-Phe (0.23 g) was obtained by using Boc-Phe-resin (2 mM, 3.85 g) as the solid-support. Synthesis, HF cleavage and purification was performed as described. Thin-layer chromatography showed $R_f$ 0.48 (silica gel glass plate, n-BuOH:pyridine:HOAc:- H₂O 15:10:3:12) and $R_f$ 0.81 (cellulose glass plate, n-BuOH:pyridine:HOAc:H₂O 15:10:3:12). Movement on electrophoresis was $R_f$ 0.53 with reference to picric acid toward the cathode. (Whatman 3MM paper, pH 1.9 formic acid-acetate buffer, 1000 V for one hour.). Amino acid analysis: 6N HCl at 110° C. for 20 hours in vacuo, Arg 1.01, Met 1.01 and Phe 1.99.

EXAMPLES 5-8

D-Phe-Met-Arg-Phe-NH₂, Phe-D-Met-Arg-Phe-NH₂, Met-Arg-Phe-NH₂ and Arg-Phe-NH₂ were synthesized and purified by methods similar to that described in Example 1. Purity of the peptide was checked by thin-layer chromatography and electrophoresis and the amino acid composition was obtained by amino acid analysis.

EXAMPLE 9

Bioassays were conducted on male Sprague-Dawley rats, weighing 250-450 g, and anesthetized by an intraperitoneal injection of a 25 percent urethane solution (1.25 g/kg). The left femoral artery was cannulated with PE 50 polyethylene tubing for monitoring of blood pressure with a pressure transducer RP-1500 (Narco Biosystems). Injections of peptides or drugs were made via a PE 10 tubing into the left femoral vein. Respiration was measured by an impedance method by which the respiratory movements of the chest are registered. The method gives indirect information on respiration amplitude. Heart and respiration frequency were obtained by using biotachometer couplers which measure mean frequencies. Body temperature was measured in the rectum with a thermistor (Yellow Springs Instruments) and maintained between 36.5° and 37.5° C. Peptides or drugs were dissolved in sterile H₂O and the volumes injected intravenously were usually 0.1 ml and never exceeded 0.2 ml.

The results of testing using various polypeptides are shown in Table I.

TABLE 1

| Peptide or amino acid | Dose-range tested (nmol/kg) | Maximal increase in blood pressure mm Hg | | Duration of blood pressure effect | No. of animals tested |
| --- | --- | --- | --- | --- | --- |
| | | systolic | diastolic | | |
| FMRF—NH₂ | 8-1000 | 100 | 75 | ++ | 10 |
| MRF—NH₂ | 44-700 | 62 | 55 | ++ | 5 |
| RF—NH₂ | 8-1000 | 76 | 65 | ++ | 11 |
| RF—OH | 32-2050 | 74 | 58 | ++ | 7 |
| F—NH₂ | 1000 | 0 | 0 | | 2 |
| D-FMRF—NH₂* | 15-500 | 45 | 35 | ++ | 3 |
| FD-MRF—NH₂* | 8-500 | 53 | 46 | +++ | 10 |
| FMD-RF—NH₂* | 500 | 0 | 0 | | 4 |
| FMRD-F—NH₂ | 1000 | 0 | 0 | | 2 |
| FMRF—OH | 33-1000 | 74 | 58 | ++ | 10 |
| R—OH | 1000 | 0 | 0 | | 2 |
| F—OH | 1000 | 0 | 0 | | 2 |
| FMRFY | 200-800 | 30 | 30 | + | 3 |
| YGGFMRF—NH₂ | 45-365 | 50 | 45 | + | 4 |
| YGGFMRF—OH | 180-365 | 35 | 30 | + | 5 |
| q MSH+ | 5-200 | 90 | 70 | +++ | 3 |

*Peptide analogs in which one L amino acid had been substituted by its respective D-stereoisomer (D-F, D-M, D-R).
+q₁MSH has a carboxyterminal RF—NH₂.
Symbols:
+ short-lasting blood pressure elevation at all doses;
++ short-lasting blood pressure elevation at low doses;
+++ long-lasting elevation at low doses.
F = Phe, M = Met, R = Arg, G = Gly, Y = Tyr.

As shown above in Table 1 the smallest peptide fragment capable of producing blood pressure elevations was Arg-Phe-NH₂. Neither arginine nor phenylalanine nor phenylalanine-amide were active. Substitution of the D-amino acid derivative in either of the last two positions resulted in a complete loss of bioactivity, whereas the presence of D-amino acids in other positions were not substantially affected. Substitution of the C-terminal phenylalanine-amide group by a tyrosine residue resulted in virtually complete loss of activity.

EXAMPLE 10

The bioassay procedure described in Example 9 was performed using a dose of 128 nmol/kg. i.v. of Phe-Met-Arg-:he-NH₂ on an anesthetized rat. FIG. 1 shows the typical effects on blood pressure, heart rate and respiration of the anesthetized rat. The elevations of blood pressure were accompanied by alternations in heart rate and breathing. The heart rate usually increased about 50-100 beats/min. At higher doses often arrhythmia developed immediately after injection causing a short-lasting drop in heart rate. Respiration movements of the thorax first decreased or stopped for 1-5 seconds and then started again with a slow and deep breathing pattern.

EXAMPLE 11

Figure 2A:
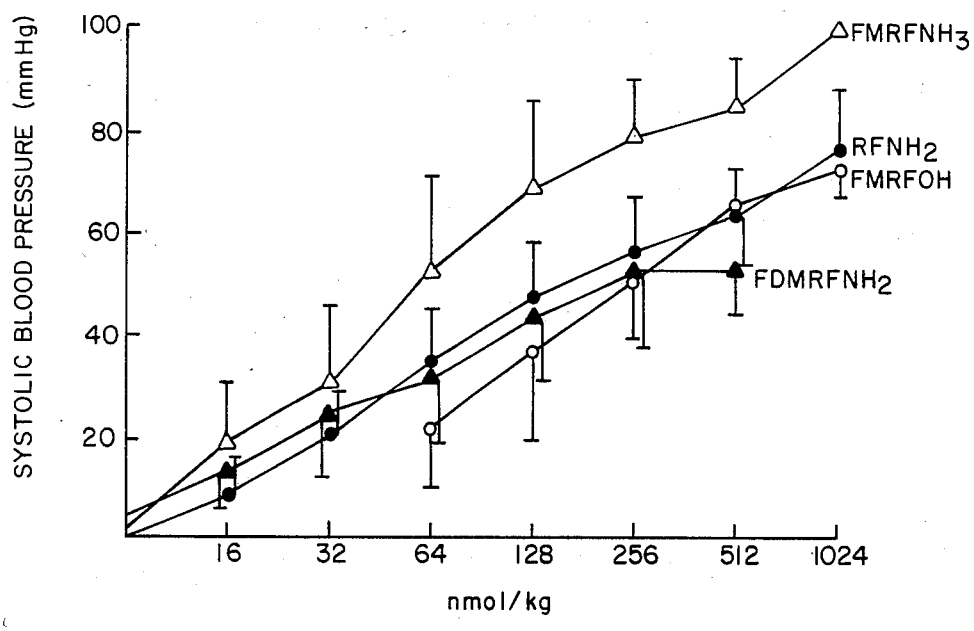

The bioassay procedure described in Example 9 was performed using various polypeptides as shown in FIGS. 2A and 2B. FIG. 2A shows the dose response relationship to systolic blood pressure for the polypeptides The-Met-Arg-Phe-NH$_2$, Arg-Phe-NH$_2$, Phe-Met-Arg-Phe, and Phe-D-Met-Arg-Phe-NH$_2$. FIG. 2B shows the time response relationship versus dosage shown in the duration of the blood pressure elevation for doses of the polypeptides Phe-D-Met-Arg-Phe-NH$_2$ and Phe-Met-Arg-Phe-NH$_2$. FIG. 2A shows that the pressor effects are dose dependent and increases of 100 mm Mercury (systolic) and 75 mm Mercury (diastolic) were observed. As shown in FIG. 2B the duration of blood pressure elevation is also dose dependent and may last from a few seconds to several minutes.

EXAMPLE 12

The pressor actions of Phe-Met-Arg-Phe-NH$_2$ were investigated by using vasodepressor drugs and standard pharmacologic antagonists. Using challenge doses of 16, 128, 512 nmol/kg FMRF-NH$_2$ injected intravenously in urethane-anesthetized rats (N≦3 per drug) 5–10 minutes after drug pretreatment, it was found that is pressor activity was not blocked by hexamethonium bromide (10–200 mg/kg i.v.), a ganglionic blocking agent; saralasin (50 to 100 µg/kg min. i.v. infusion), an angiotensin I converting enzyme inhibitor; (1-($\beta$-mercapto-$\beta$,$\beta$-cyclopentamethylene propionic acid), 2-(0-methyl)tyrosine)Arg$^8$-Vasopressin 10 µg/kg, a vasopressin antagonist (14); or propanol hydrochloride (0.1 to 1 mg/kg), a $\beta$-adrenergic receptor antagonist. Saralsin and 1-($\beta$-mercapto-$\beta$,$\beta$-cyclopentamethylene propionic acid, 2-(0-methyl)tyrosine)Arg$^8$-Vasopressin were effective antagonists when their respective agonists, angiotensin II (2 µg/kg, and Arg$^8$-vasopressin (1 µg/kg) were used. Drugs which interact with the $\alpha$-adrenergic system (phentolamine hydrochloride 5 to 10 mg/kg; tolazoline hydrochloride 3 to 15 mg/kg; dihydroergotamine mesylate 0.05 to 1 mg/kg; clonidine hydrochloride 1 to 100 µg/kg differentially attenuated the FMRFamide effect by about 30–75%. Lower doses of phentolamine hydrochloride and tolazoline hydrochloride, effective at blocking the pressor effects of norepinephrine hydrochloride 3 to 15 µg/kg, did not affect FMRFamide. Phenoxybenzamine hydrochloride (0.03 to 0.3 mg/kg), a specific $\alpha$-antagonist had no effect on the pressor activity. These results suggest an indirect interaction between FMRFamide and the $\alpha$-adrenergic vasoconstrictor system. Other drugs: reserpine 0.5 to 5 mg/kg, given either 24 hours i.p. or 10–60 min. i.v. prior to FMRF-NH$_2$; nalozone hydrochloride 1 mg/kg; nitroprusside 192 µg/kg min. i.v. infusion; cyproheptadine 1 mg/kg; and atropine 1 to 10 mg/kg, did not modify the pressor effects of FMRFamide.

EXAMPLE 13

The pressor effects of Phe-Met-Arg-Phe-NH$_2$ were not modified in adrenalectomized animals as shown in FIG. 3. The data for the adrenalectomized rats is showns by a solid line connected by circles. In hypophysectomized animals (data shown by solid line connected by X's), a slight reduction was found in the medium dosage range. The dotted curve is the behavior of sham hypophysectomized rats and the curve connected by triangles is that of Phe-Met-Arg-Phe-NH$_2$. From the data in FIG. 3 it may be surmised that Phe-Met-Arg-Phe-NH$_2$ does not produce pressor effects by acting via a recognized vasoconstrictor pathway.

What is claimed is:

1. A method of elevating blood pressure in a mammal comprising the step of administering to said mammal an effective amount of a compound sufficient to induce blood pressure elevation, said compound selected from the group consisting of gamma$_1$-melanotropic stimulating hormone, Tyr-Gly-Gly-Phe-Met-Arg-Phe-NH$_2$, D-Phe-L-Met-L-Arg-L-Phe-NH$_2$, L-Phe-D-Met-L-Arg-L-Phe-NH$_2$, D-Phe-D-Met-L-Arg-L-Phe-NH$_2$, L-Met-L-Arg-L-Phe-NH$_2$, and L-Phe-L-Met-L-ARg-L-Phe.

2. A method according to claim 1 wherein said polypeptide is $\gamma_1$-melanotropic stimulating hormone.

3. A method according to claim 1 wherein said polypeptide is Tyr-Gly-Gly-Phe-Met-Arg-Phe-NH$_2$.

4. A method according to claim 1 wherein said polypeptide is L-Phe-L-Met-L-Arg-L-Phe.

* * * * *